United States Patent [19]

Germanas et al.

[11] 3,962,367

[45] June 8, 1976

[54] OLEFIN ISOMERIZATION USING A COBALT-SULFUR CATALYST

[75] Inventors: Dalia Germanas, Des Plaines; Ernest L. Pollitzer, Skokie, both of Ill.

[73] Assignee: Universal Oil Products Company, Des Plaines, Ill.

[22] Filed: Mar. 24, 1975

[21] Appl. No.: 561,455

Related U.S. Application Data

[62] Division of Ser. No. 407,125, Oct. 17, 1973, Pat. No. 3,898,179.

[52] U.S. Cl. .............................................. 260/683.2
[51] Int. Cl.$^2$ .............................................. C07C 5/22
[58] Field of Search ................................. 260/683.2

[56] References Cited
UNITED STATES PATENTS

| | | | |
|---|---|---|---|
| 3,271,475 | 9/1966 | Weesner | 260/683.2 |
| 3,542,896 | 11/1970 | Butte | 260/683.2 |
| 3,542,898 | 11/1970 | Butte | 260/683.2 |
| 3,634,540 | 1/1972 | Wang | 260/683.2 |
| 3,721,718 | 3/1973 | Hughes | 260/683.2 |
| 3,821,123 | 6/1974 | Germanas | 260/683.2 |
| 3,845,152 | 10/1974 | McKenna | 260/683.2 |

Primary Examiner—Veronica O'Keefe
Attorney, Agent, or Firm—James R. Hoatson, Jr.; Thomas K. McBride; William H. Page, II

[57] ABSTRACT

Double bond isomerization of olefins utilizing a catalyst comprising cobalt and sulfur on a porous carrier; the catalyst being prepared by forming an initial composite of the cobalt with the carrier material, sulfiding the initial composite to provide a sulfur/cobalt atomic ratio of at least about 1 in the sulfided composite, and then stripping sufficient sulfur from the sulfided composite with hydrogen to provide a final isomerization catalyst composition having a sulfur/cobalt atomic ratio of less than about 1 and more than about 0.55.

3 Claims, No Drawings

OLEFIN ISOMERIZATION USING A COBALT-SULFUR CATALYST

RELATED APPLICATION

The present application is a division of my copending application, Ser. No. 407,125 filed Oct. 17, 1973, now U.S. Pat. No. 3,898,179, all the teachings of which are incorporated herein by specific reference thereto.

BACKGROUND OF THE INVENTION

This invention relates to a process for isomerizing the double bond in olefins to provide different, isomeric olefins.

This invention also relates to a novel catalyst composition useful as a catalyst for olefin double bond isomerization.

This invention further relates to a process for isomerizing the double bond of an olefin without undesirable polymerization or skeletal isomerization.

A number of catalysts capable of isomerizing the double bond of an olefin are known in the art. Such catalysts are capable, for example, of converting butene-1 to butene-2, the 2-isomer being more valuable commercially than the 1-isomer. Many of the previously known catalysts have been found deficient in various ways, especially where they are employed under commercial operating conditions.

One serious drawback found in many previously disclosed olefin isomerization catalysts is their lack of selectivity. In an olefin isomerization operation, the catalyst must be selective for the double bond shift. For example, when it is desired to convert butene-1 to butene-2 a more valuable chemical, the catalyst must be capable of selectively catalyzing this double bond shift without converting the butene-1 to other compounds such as polybutenes, isobutylene, n-butane, or lower molecular weight hydrocarbons. In this case, selectivity refers to the ability of the catalyst to isomerize the double bond in the reactant without causing the reactant compound to polymerize, crack or hydrogenate, or causing carbon chain rearrangement in the reactant compound.

In order for a double bond shift catalyst to be commercially acceptable, it must be active for the desired double bond shift at temperatures at which equilibrium between double bond isomers favors conversion to the desired double bond isomer, while remaining inert with respect to other compounds commingled with the reactant compound during the isomerization reaction. The olefins which it is desired to isomerize in commercial operations are generally available only in admixture with other hydrocarbons. For example, in all economically feasible sources of butene-1, it is available only in admixture with isobutylene. Because of the very similar boiling points of butene-1 and isobutylene, it is completely impractical to attempt to separate butene-1 from isobutylene by fractionation. Butene-2, on the other hand, can economically be separated from butene-1 and isobutylene by fractionation. Thus, in commercial operation for isomerizing butene-1 to provide butene-2, the butene-1 feed to the isomerization operation always contains a significant amount of isobutylene. In order to utilize an olefin isomerization catalyst in such an isomerization operation, the catalyst must be capable of catalyzing the conversion of butene-1 into butene-2 at temperatures where butene-2 is favored by equilibrium, while remaining inert to the isobutylene. It is well known in the art that certain olefins, particularly isobutylene, polymerize very readily to form high molecular weight hydrocarbons. Heretofore, it has been difficult to convert butene-1 into butene-2 in the presence of isobutylene without causing polymerization of the isobutylene. Except for di-isobutylene, the polymers of isobutylene are of very little economic utility, while isobutylene itself is valuable as, for example, a feed stock for use in isoparaffin-olefin alkylation operations. It is therefore undesirable to polymerize the isobutylene during an operation to isomerize the butene-1 to provide butene-2.

Because of the relative lack of success in using previously known catalysts to provide a stable isomerization operation while remaining active and selective at temperatures favorable to high olefin conversion rates, previous attempts to provide an olefin double bond isomerization process have generally not been completely successful. The process of the present invention overcomes selectivity and stability difficulties and provides a practical and desirable method for shifting the double bond in olefinic hydrocarbons.

SUMMARY OF THE INVENTION

It is an object of the present invention to provide a catalyst suitable for double bond isomerization of olefinic hydrocarbons.

Another object of the present invention is to provide a process for double bond isomerization of olefins.

Another object of the present invention is to provide an olefin isomerization catalyst which is selective for double bond isomerization of olefins.

Another object of this invention is to provide an olefin isomerization catalyst which possesses high activity for double bond isomerization.

A further object of this invention is to provide an olefin double bond isomerization catalyst which possesses stability of performance at high rates of conversion.

Another object of the present invention is to provide an olefin isomerization catalyst capable of converting butene-1 to provide butene-2 in the presence of isobutylene without causing polymerization of the isobutylene, and without rapid deactivation of the catalyst.

Another object of the present invention is to provide a process for isomerizing butene-1, while in admixture with isobutylene, to provide butene-2, without polymerizing the isobutylene.

Therefore, in an embodiment, the present invention relates to an olefin isomerization catalyst comprising a combination of a sulfur component and a catalytically effective amount of a cobalt component with a porous carrier material, the catalyst containing less than about 1 mole and more than about 0.55 mole of sulfur per mole of the cobalt component, calculated as the elemental metal, said catalyst being prepared by the steps of: forming an initial composite of the cobalt component and the carrier material, the cobalt component being present in the initial composite in a form selected from the elemental metal or the oxide; sulfiding the initial composite by contacting same with a sulfide yielding compound at sulfiding conditions to provide a sulfided composite containing at least about 1 mole of sulfur per mole of the cobalt component in the sulfided composite; and, stripping sulfur from the resulting sulfided composite with a hydrogen-containing gas at stripping conditions to provide the olefin isomerization catalyst, sufficient sulfur being stripped from the sulfided composite to provide a sulfur content in the catalyst of less than about 1 and more than about 0.55 mole of sulfur per mole of the cobalt component in the catalyst.

In another embodiment, the present invention relates to a process for isomerizing an isomerizable olefin which comprises contacting the olefin, at olefin isomerization conditions, with an olefin isomerization catalyst comprising a combination of a sulfur component and a catalytically effective amount of a cobalt component with a porous carrier material, the catalyst containing less than about 1 and more than 0.55 mole of sulfur per mole of the cobalt component, calculated as the elemental metal, the catalyst being prepared by the steps of: forming an initial composite of the cobalt component and the carrier material, the cobalt component being present in the initial composite in a form selected from the elemental metal or the oxide; sulfiding the initial composite by contacting same with a sulfide yielding compound at sulfiding conditions to provide a sulfided composite containing at least about 1 mole of sulfur per mole of the cobalt component in the sulfided composite; and stripping sulfur from the resulting sulfided composite with a hydrogen-containing gas at stripping conditions to provide the olefin isomerization catalyst, sufficient sulfur being stripped from the sulfided composite to provide a sulfur content in the catalyst of less than about 1 and more than about 0.55 mole of sulfur per mole of the cobalt component in the catalyst.

By employing the catalyst and processing conditions more fully described hereinafter, isomerizable olefins can be converted to different, isomeric olefins with a very high yield of the desired isomeric olefins. The catalyst of the present invention exhibits none of the undesirable characteristics of many catalysts, such as instability and lack of selectivity. Thus, isomerizable olefins may be converted to different, isomeric olefins, using the present process, without cracking, hydrogenation or polymerization of the reactant olefin, without rapid deactivation of the catalyst, and without adverse effects on any other hydrocarbons present during the isomerization operation. For example, butene-1 may be isomerized, while in admixture with isobutylene, to provide essentially equilibrium conversion of the butene-1 into butene-2, without the occurrence of any adverse side reactions such as polymerization of isobutylene, hydrogenation of butenes, or skeletal isomerization of any hydrocarbons in the feed stock. Moreover, the foregoing is accomplished under very moderate conditions of operation, providing savings in the capital and utilities requirements in commercial embodiments of the process.

DETAILED DESCRIPTION OF INVENTION

One essential feature of the present invention is a catalyst composition containing cobalt and sulfur on a porous carrier material, or support, which exhibits surprising selectivity and stability when employed as a catalyst for double bond isomerization of olefins. The method of preparation of the composition is a critical factor in insuring that the composition possesses the desired high isomerization activity while, at the same time, exhibiting excellent stability over long periods of use and surprising inertness to diluent hydrocarbons, even in the presence of very easily polymerizable diluent materials such as isobutylene.

The first step in the preparation of the catalytic composition of the present invention is the formation of an initial composite of the cobalt component with the porous carrier material. The cobalt component in the initial composite is in the form of reduced cobalt, i.e., the elemental metal, or else is in the form of cobalt oxide. Either the oxide or elemental metal may be used with equivalent results. The amount of cobalt in the initial composite, calculated on the basis of the elemental metal, is between about 5 weight percent and about 80 weight percent of the total weight of the initial composite, with a preferred range of cobalt content being about 10 weight percent ot about 60 weight percent of the total initial composite.

The porous carrier material employed in the present catalyst composition is relatively inert and refractory under the condition employed in the isomerization operation. A variety of suitable support materials may be employed in the catalyst. For example, any of the following may be utilized to provide the porous carrier material within the scope of this invention: activated carbon, coke or charcoal; silica, silica gel, synthetic or naturally occurring silicates such as kieselguhr, attapulgus clay, china clay, fullers earth, kaoline, etc., and refractory inorganic oxides such as alumina, titania, zirconia, chromia, zinc oxide, magnesia, thoria, boria, etc., as well as mixtures and combinations of the above. The preferred porous carrier materials are refractory inorganic oxides, especially silica, alumina, and kieselguhr.

The initial composite of the cobalt component and the carrier material may be prepared in any suitable conventional manner. For example, the carrier may be formed into spheres or pellets, extruded, etc. The cobalt component is then impregnated thereon by contacting the carrier with a solution of a soluble and heat-decomposable cobalt compound, and evaporating the solute, leaving a cobalt compound deposited on the carrier. The composite is then heated to decompose the cobalt compound, the cobalt being converted into the oxide or elemental metal, depending upon the heating medium. Another suitable method for preparing the initial composite of the cobalt component and the porous carrier material is by co-extrusion. In this operation, an aqueous refractory inorganic oxide sol is admixed with a water-soluble cobalt compound such as cobalt nitrate, cobalt sulfate or cobalt chloride. The aqueous mixture is then combined with an aqueous alkaline solution of, for example, ammonium hydroxide, ammonium carbonate, or the like, to precipitate a mass of finely-divided particles. The mass of particles produced is then partially dried and compressed or extruded by conventional means to form pills, pellets, etc. The extruded particles are then heated and dried to convert the cobalt to the elemental metal or oxide. Various other known methods for forming the initial composite of cobalt component and carrier are also suitable, including, for example, forming a mixture of dry, finely-divided particles of the porous carrier with finely-divided particles of cobalt or a cobalt compound, compressing the mixture into pills or pellets, and heating, if necessary to decompose the cobalt compound to the oxide or elemental metal.

One preferred method for forming the initial composite of the cobalt component with the carrier includes treating inorganic oxide particles with an aqueous solution of a soluble cobalt compound. Generally, the inorganic oxide particles utilized will have been basic aged and water washed. For example, the inorganic gel particles may comprise spheroidal particles of uniform physical characteristics formed by dispersing an inorganic oxide hydrosol in the form of droplets into a suitable gelling medium and immediately thereafter subjecting the resulting gel spheres to an aging treatment in a basic medium. The gelling medium may be any suitable water immiscible suspending liquid, usually a light gas oil chosen principally for its high interfacial tension with respect to water. Basic aging is usually accomplished by initially commingling a weak base, such as urea, hexamethylenetetramine, and the like, with the hydrosol before dispersing the same in the gelling medium as described above. During the subsequent aging process, the weak base retained in each gel particle continues to hydrolize, forming ammonia and carbon dioxide. Generally, the spheres are retained in the gelling medium at a temperature of 120°F. to 210°F. in a separate vessel to complete the aging process. The aging process usually further comprises an aqueous ammonia treatment before a final water wash to remove soluble matter. The basic aged, water washed, spherical gel particles, with extraneous water decanted or filtered therefrom, are then calcined at about 400°C., usually in an air atmosphere, and subsequently further treated with a solution of a soluble compound of cobalt such as cobalt nitrate, cobalt sulfate, cobalt chloride, or cobalt acetate. The particles are soaked in the water-soluble cobalt compound solution for about 1 to about 2 hours at room temperature and thereafter evaporated to dryness in for example a rotary steamed dryer. The dried composite is then heated at about 100°C. to about 300°C. for 1 to 2 hours. If the heating is performed in an air atmosphere, the resulting initial composite of cobalt component and carrier material will contain cobalt in the form of the oxide.

Another preferred method of preparing the initial composite of the cobalt component with the carrier, when the carrier material is kieselguhr or the like, is by adding a hot aqueous solution containing the required amount of cobalt sulfate or nitrate to a suspension of kieselguhr and water and subsequently heating the resultant mixture at a temperature of about 60° to about 80°C. with stirring while a hot aqueous solution of sodium carbonate is added thereto with stirring to precipitate cobalt carbonate upon the kieselguhr. This precipitation is usually carried out at a temperature of about 60° to about 80°C. and particularly good results are obtained at about 70°C. It has been found desirable to add about 1.7 molar proportions of sodium carbonate per atomic portion of total cobalt ions in order that the finished catalyst will have the desired consistency. The mixture of cobalt carbonate and kieselguhr may then be separated from the aqueous solution by filtration. The solid material is dried, mixed with about 4% by weight of finely-divided graphite to act as a pelleting lubricant, and formed into pellets by, for example, a pilling machine. The pelleted material may then be heated in air at about 300° to about 400°C. to decompose the cobalt carbonate into cobalt oxide. After the evolution of carbon dioxide has substantially ceased, the resultant mixture of cobalt oxide and kieselguhr may be utilized directly as the initial composite, or the cobalt may be converted to the elemental metal by heating the composite in a stream of hydrogen at a temperature up to about 550°C.

The next essential step in producing the catalytic composition, after the formation of the initial composite of the cobalt component with the carrier material, is sulfiding of the composite to produce a sulfided composite containing at least about one mole of sulfur per mole of cobalt, i.e., the initial composite is subjected to sulfiding conditions sufficient to provide the sulfided composite with a sulfur/cobalt atomic ratio of about 1 or more. The initial composite is sulfided by contacting it with a sulfide-yielding compound at sulfiding conditions. The sulfide-yielding compound utilized in this step may be any inorganic or organic sulfide containing compound capable of producing cobalt sulfide when contacted with the initial composite of the cobalt component and carrier material at sulfiding conditions. One suitable sulfide-yielding compound is hydrogen sulfide. Ammonium sulfide, ammonium hydrosulfide, the alkyl and aryl mercaptans, organic and inorganic soluble sulfides and organic thioethers, disulfides, thioaldehydes, thioketones and the like sulfur-containing compound may also be employed, although not necessarily with equivalent results. Although the sulfiding step may in some cases be performed under liquid phase conditions, the preferred procedure involves contacting a gas stream containing the sulfide-yielding compound with the initial composite. Accordingly, the sulfide-yielding compounds that are more preferred are volatile at the hereinafter specified sulfiding conditions. In general, best results in the sulfiding step have been obtained when the sulfide-yielding compound is hydrogen sulfide in solution in a major portion of hydrogen. The sulfiding conditions utilized are selected to produce a reaction between the cobalt component of the initial composite and the sulfur-containing sulfiding material in order to form a cobalt sulfide-containing composite. Ordinarily, temperatures ranging from about 10°C. up to about 550°C. or more are operative, with the preferred temperatures being about 20°C. to about 450°C. when hydrogen sulfide is utilized. The temperature employed may vary, depending on the strength of the sulfiding agent, etc. The pressure utilized can be selected from an extremely broad range and does not greatly effect the course of the sulfiding step. Ordinarily, atmospheric or subatmospheric pressures can be utilized with good results. It is ordinarily preferred to continue the sulfiding operation until the composite no longer reacts with the sulfide yielding compound.

A preferred method for sulfiding the initial composite is by passing a mixture of hydrogen sulfide and hydrogen over the initial composite. Good results are obtained when the amount of hydrogen sulfide is between about 5% and about 30% of the hydrogen in the mixture. The temperature maintained during the preferred sulfiding operation is about 20°C. to about 450°C. The gaseous hydrogen sulfide-hydrogen mixture is preferably passed over the composite at the rate of about 250 cc. to about 1000 cc. per minute per 100 cc. of composite. The sulfiding operation is continued until the amount of sulfur in the composite, in the form of the sulfide, is at least about 1 mole of sulfur per mole of cobalt in the composite. Excess hydrogen sulfide is then purged from the sulfided composite.

The third essential step in producing the catalytic composite of the present invention, after formation of the initial composite of the cobalt component and the porous carrier and sulfiding of the initial composite, is the removal of sulfur from the sulfided composite by stripping the sulfided composite with a hydrogen-containing gas at stripping conditions to provide the catalyst utilized in the present isomerization operation. The gas utilized in the stripping operation may be pure hydrogen or may be a mixture of hydrogen with gases substantially inert in the stripping operation such as nitrogen, argon, etc. Pure hydrogen gas is preferred for use. The stripping operation generally includes continuously passing the hydrogen-containing gas over the sulfided composite, but may also be conducted in a batch-type operation in which a quantity of hydrogen-containing gas is contacted with the particular quantity of sulfided composite to be stripped for a specified period of time at the desired temperature and pressure, and the gas is subsequently purged or otherwise removed from contact with the stripped composite. In such a batch-type operation, a large number of repetitions of the operation will generally be required. A continuous stripping operation is preferred because of its obviously greater ease of operation and more rapid results in stripping sulfur from the sulfided composite to form the desired catalyst composition. The continuous operation includes continuously passing a stream of hydrogen-containing gas, preferably pure hydrogen, over the sulfided composite. The stripping operation can be performed in a fairly broad temperature range, e.g., to about 200°C. to about 600°C. or more. In order to determine the amount of sulfur stripped from the sulfided composite, the amount of sulfur in the sulfided composite can be determined by analysis before commencing the stripping operation. The stripping operation is then started and continued, with the amount of sulfur removed being continuously determed by analysis of the hydrogen-containing gas stream after it is passed over the sulfided composite. Preferably, the hydrogen-containing gas is passed over the sulfided composite at the rate of about 250 cc. to about 2000 cc. per minute of hydrogen per 100 cc. of the sulfided composite. Preferably a temperature of about 300°C. to about 600°C. or more is maintained during the stripping operation, with a temperature of about 400°C. to about 600°C. especially preferred. At stripping temperatures higher than 600°C. the porous carrier material employed in the composite may suffer deleterious results, especially from prolonged stripping operations. Generally, the amount of sulfur which can be stripped away from the sulfided composite is relatively small. It is very difficult to strip enough sulfur from the sulfided composite to provide a final catalyst having less than about 0.7 mole of sulfur per mole of cobalt. The time and temperatures involved in stripping enough sulfur from the composite to obtain a final sulfur/cobalt mole ratio less than 0.55 substantially prohibit forming a final catalyst having such a composition. Since excellent results can be obtained using a catalyst having sulfur/cobalt mole ratios as high as 0.8 to 0.9 and higher, the preferred ratio is about 0.7 to about 0.9. After the desired amount of sulfur has been stripped from the sulfided composite so that less than 1 mole and greater than 0.55 mole of sulfur remains in the composite per mole of cobalt in the composite, calculated as the elemental metal, the stripping operation is discontinued and the final catalytic composite is then ready for use in the isomerization operation of the present invention. The cobalt in the finished catalyst should be present in a catalytically effective amount, generally about 5 weight percent to about 80 weight percent of the finished catalyst. A preferred range of cobalt content in the finished catalyst is about 10 weight percent to about 60 weight percent.

The catalyst of the present invention can in general be employed in the isomerization of the olefinic double bond of a variety of olefins. Olefins which may be isomerized using the process of the present invention include generally all mono-olefins in which the olefinic bond is shiftable to convert the olefin to a different isomeric olefin. Specific isomerizable olefins include butene-1, butene-2, methylbutenes and n-pentenes, hexenes, decenes, etc. The present process produces essentially equilibrium conversion of an isomerizable reactant olefin. For example, use of a particular butene or pentene isomer as the reactant olefin in the present process will convert the reactant olefin to an equilibrium mixture of butene double bond isomers to pentene double bond isomers, respectively.

The preferred olefins for use in the present isomerization process are butenes. It is well-known in the art that butene-1 is only available on a commercial scale commingled with at least some isobutylene. This is primarily because of the similar boiling point of butene-1 and isobutylene, which render their separation by fractionation infeasible. The commercial operations which are the only available sources of $C_4$ olefins, e.g., fluid catalytic cracking and thermal cracking operations, provide butene-1 and butene-2 supplies which contain at least about 10–20% isobutylene, while the amount of isobutylene in the $C_4$ olefin supplies produced in these operations is often as high as 50–60% of the $C_4$ olefins content. Butene-2, which is more valuable as a chemical precursor than butene-1, can be separated from the other two $C_4$ olefin isomers by fractionation, so that by isomerizing the butene-1 fraction it is then possible to recover substantially all the linear $C_4$ olefins as butene-2 by fractionating the $C_4$ olefins to separate butene-2 from isobutylene and butene-1. The isobutylene and butene-1 can be recycled to the isomerization operation so that substantially all of the butene-1 can be converted to butene-2 and subsequently separated from the isobutylene. In such an operation, a drag stream containing a high concentration of isobutylene must be removed from the recycle stream containing butene-1 and isobutylene in order to prevent a buildup of isobutylene in the operation.

An olefin to be isomerized in the process of the present invention may be utilized in the form of a pure compound or may be admixed with other olefins, saturated hydrocarbons, aromatics, etc., or any other material which is relatively inert at the isomerization conditions employed. Commercially available olefin feed stocks generally contain the reactant olefin in admixture with at least once saturated hydrocarbon, since, in order to obtain all the reactant olefin from the source, at least some saturated hydrocarbons are unavoidably recovered because of imprecise fractionation and economic limitations. Such saturate-diluted feed stocks are generally preferred for use in the present process. For example, commercial sources of butene-1 generally supply the butene-1 in admixture with saturated hydrocarbons such as propane, isobutane, etc. The primary commercial sources of butene-1 are catalytic and thermal petroleum cracking operations. A typical butene-1 feed stock supplied to the present isomerization process from such a cracking operation might contain 30–70 vol.% isobutane and/or propane. Such a feed stock is suitable for use in the present process. As described above, isobutylene is almost invariably present in commercially available supplies of butene-1. For example, a typical fluid catalytic cracking operation might supply a butene-1 feed stock suitable for use in the present process which contains 5 vol.% propane, 10 vol.% butene-1, 15 vol.% butene-2, 25 vol.% isobutylene, and 45 vol.% isobutane. It is apparent from this example that a process for isomerizing the butene-1 component of such a feed stock must necessarily be inert for other than the desired reaction because of the other hydrocarbons present in the feed stock.

Olefin isomerization conditions useful in the process of the present invention include a temperature of about 25°C. to about 200°C. The preferred temperature range is from about 75°C. to about 160°C. Although isomerization can be effected when the present process is performed using liquid phase operations, it has been found that the catalyst of the present invention deactivates fairly rapidly unless vapor phase operations are maintained. Thus, the pressure preferred in the present process is that chosen to provide vapor phase operations at the particular temperature desired for use. In general, a pressure of subatmospheric to about 30 atmospheres is satisfactory. Normally the operation should be conducted with the temperature and pressure above the dew point of the least volatile component of the olefin-containing feed stock employed in the process. The reaction times utilized in the present process are preferably calculated, in general, on the basis of the volume of olefinically unsaturated hydrocarbons (excluding propylene) which are contacted with the catalyst. For example, using a feed stock containing propane, butene-1, isobutylene, butadiene and isobutane, the reaction time is preferably calculated on the basis of the volume of combined butene-1, isobutylene and butadiene employed. In a preferred, continuous operation, the space velocity used is referred to as the "olefin space velocity" which is intended to describe the space velocity of all $C_4$ and heavier olefinically unsaturated hydrocarbons in the feed stock employed, irrespective of the exact amounts of saturates, hydrogen, etc., which are utilized. Thus, in the preferred continuous operation, an olefin liquid hourly space velocity (liquid volume of $C_4$ and heavier olefin per hour per volume of catalyst employed) of about 0.5 to about 20 may suitably be employed. An olefin liquid hourly space velocity of about 1 to about 10 is preferred. At lower space velocities, a lower temperature may generally be employed. The space velocity and temperature are normally adjusted according to the content of the feed stock to give high conversions at the highest possible space velocity with vapor phase operations. Some hydrogen is required in the operation for satisfactory performance. At least about 0.01 mole of hydrogen should be charged to the isomerization operation for every mole of unsaturates charged, and preferably about 0.1 mole of hydrogen is used for each mole of charge stock. More hydrogen may be required when large amounts of sulfur and/or polyolefins such as butadiene are present in the olefin feed stock employed. One significant advantage of the present process is that the isomerization operation is not adversely effected by fairly high water levels in the feed stocks employed. For example, a water level of 200 ppm. in the feed has substantially no effect on the operation.

The isomerization process of the present invention may be performed using any suitable reactor known to the art. A batch-type operation may be employed, in which a fixed portion of the olefin-containing feed stock and a specific amount of the catalyst of the present invention are placed in an appropriate vessel, such as an autoclave, and contacted therein for an appropriate length of time. The isomerized charge stock is then withdrawn from the vessel and the isomerized olefin product is recovered. The preferred mode of operation is a continuous-type operation. The catalyst may be utilized as a fixed bed, with the hydrocarbon charge stock continuously being passed over the bed. The catalyst may also be employed in a moving-bed operation including both countercurrent and co-current operations. The preferred mode of operation is a continuous, fixed-bed operation in which the reactant olefin is continuously passed into the reactor and downwardly over a fixed bed of the catalyst and then withdrawn continuously from the reactor. A large variety of reactors suitable for use in the present process will be obvious to those skilled in the art from the foregoing.

ILLUSTRATIVE EMBODIMENT I

In order to illustrate a preferred method of preparation of the catalyst of the present invention, the following illustration is presented. The initial composite of the cobalt component with the carrier material is prepared by the following method. An alumina sol is emitted as droplets into an oil suspending medium maintained at a temperature of about 100°C. and aging the resultant spherical particles for a 24 hour period. The aforesaid alumina sol has been prepared by digesting aluminum pellets in hydrochloric acid to maintain an aluminum/chlorine ratio of 1.38, the sol containing 13.5 wt.% aluminum. Upon completion of the aging period the spherical gel particles are recovered and washed with a 0.05 wt.% ammonium nitrate solution of 90°C. The pH of the washed solution is 9.5. The particles are then dried and calcined in an air atmosphere for 1 hour. A solution of 1660 grams of cobalt nitrate hexahydrate and 350 cc. of 28% ammonia solution in 1500 cc. of water is made up. 1,000 grams of the alumina spheres are placed in the impregnating solution. The particles are soaked for about 1 hour at room temperature and thereafter evaporated to dryness in a rotary steam dryer. The dried composite is heated at 200°C. for 1 hour in an air atmosphere. The resulting composite is analyzed and the cobalt content is determined to be 25 weight percent, calculated as the elemental metal.

The initial composite of cobalt with the alumina carrier is then sulfided. A 10% solution of hydrogen sulfide and hydrogen is passed over 1,000 grams of the initial composite at the rate of 5 liters (at standard conditions) per hour at a temperature of 400°C. until the hydrogen sulfide no longer reacts with the composite. The sulfided composite is then analyzed and found to contain 13 weight percent sulfur. The sulfur/cobalt mole ratio in the sulfided composite is found to be 1.1. The sulfided composite is then stripped with hydrogen by passing 5 liters (at standard conditions) of hydrogen per hour over the sulfided catalyst at a temperature of 400°C. for four hours. The stripped catalyst is then analyzed. It is found to contain 10.9 weight percent sulfur and 22.3 weight percent cobalt. The sulfur/cobalt mole ratio in the finished catalyst is found to be 0.9. This catalyst, prepared according to the present invention, is designated Catalyst A. In order to demonstrate the superiority of the catalyst of the present invention over conventional catalysts, two more catalysts are prepared. A composite containing 25 weight percent cobalt on an alumina carrier is prepared by a method identical to that used to produce the initial composite used to prepare Catalyst A. Alumina spheres are calcined at 600°C. and then impregnated with a cobalt nitrate solution. The composite is dried in a rotary steam dryer and heated to 200°C. in air. The cobalt in this composite is reduced by passing hydrogen over the composite at a temperature of 400° until all the cobalt in the composite is in the form of the reduced metal. The resulting composite of reduced cobalt on an alumina support is designated Catalyst B. A third composite of cobalt on an alumina support is prepared in a manner identical to that used to prepare Catalysts A and B. First, a composite containing 25 weight percent cobalt on the alumina spheres is made up by impregnating the spheres with the cobalt nitrate solution, drying, and then calcining in air at 600°C. The composite is then sulfided in a procedure identical to the one used to sulfide Catalyst A, by passing a ten percent solution of hydrogen sulfide in hydrogen over the composite at a temperature of 400°C. until the hydrogen sulfide no longer reacts with the composite. The sulfided composite is then analyzed and the sulfur/cobalt mole ratio is found to be 1.1. This catalyst is designated Catalyst C.

ILLUSTRATIVE EMBODIMENT II

Catalyst A, prepared according to the method of the present invention, is compared to Catalysts B and C in a vapor phase butene-1 isomerization operation. A charge stock containing 55 mole percent propane, 30 mole percent butene-1 and 15 mole percent isobutylene is employed. Equal quantities of Catalysts A, B and C are utilized in fixed-bed operations in identical isomerization reactors. Equal portions of the charge stock are continuously passed through the bed of each catalyst at an olefin liquid hourly space velocity of 2. A pressure of 200 psig. and a temperature of 140°C. are maintained in each reactor. Small equal amounts of hydrogen are also passed continuously into each reactor in admixture with the portions of charge stock. The effluents from each reactor are separately collected and analyzed. Catalyst A is found to achieve a high initial rate of conversion (50–90 mole percent) of butene-1 to butene-2 in initial operation, with no detectable polymerization of isobutylene. Catalyst B also exhibits a high initial conversion rate equivalent to that found in Catalyst A, but a small amount of isobutylene polymerization is found to occur using Catalyst B. Catalyst C exhibits a low rate of conversion (10–20 mole percent) of butene-1 to butene-2 in initial operation. After 300 hours of operation at the above-specified condition, the effluents from the three reactors are again analyzed. Catalyst A is found to be extremely stable, and is still able to provide the same high rate of conversion of butene-1 to butene-2, substantially the same as in initial operation, with no signs of a decrease in conversion or selectivity. Catalyst B is found to be unstable. After 300 hours of operation, the rate of conversion of butene-1 to butene-2 found to be provided by Catalyst B has decreased to about one-half of the initial conversion rate, and is found to be continuously decreasing further. The conversion rate of catalyst is now much lower than that of Catalyst A. Catalyst C is found to have the same low conversion rate as in initial operation.

As demonstrated by the foregoing detailed description of the invention and illustrative embodiments, the catalyst and process of the present invention provide a superior method for double bond isomerization of isomerizable olefins, particularly when it is found necessary to perform the isomerization operation with the reactant olefin in admixture with one or more easily polymerizable hydrocarbons. Thus, the catalyst of the present invention provides an isomerization operation in which the catalyst exhibits surprising stability while providing a high rate of conversion with substantially no side reactions and polymerization of commingled easily polymerizable hydrocarbon.

We claim as our invention:

1. A process for isomerizing an isomerizable olefin by shifting the olefinic bond therein which comprises contacting said olefin at olefin isomerization conditions with a catalyst composite of a sulfur component and from about 5 to about 80 weight percent of a cobalt component with a porous carrier material, said catalyst containing less than about 1 mole and more than about 0.55 mole of said sulfur component per mole of said cobalt component, calculated as the elemental metal, said catalyst having been prepared by the steps of:
    a. forming an initial composite of said cobalt component and said carrier material, said cobalt component being present in the initial composite as the elemental metal or the oxide;
    b. sulfiding said initial composite by contacting same with a sulfide-yielding compound at sulfiding conditions to provide a sulfided composite containing at least about 1 mole of sulfur per mole of said cobalt component in the sulfided composite; and,
    c. stripping sulfur from the resulting sulfided composite with a hydrogen-containing gas at stripping conditions, sufficient sulfur being stripped from said sulfided composite to provide a sulfur content in said catalyst of less than about 1 mole and more than about 0.55 mole of sulfur per mole of said cobalt component in the catalyst.

2. A process according to claim 1 further characterized in that said olefin is butene-1.

3. A process according to claim 1 further characterized in that said olefin isomerization conditions include a temperature of about 25°C. to about 200°C., a pressure of subatmospheric to about 30 atmospheres, and an olefin liquid hourly space velocity of about 0.5 to about 20.

* * * * *